(12) United States Patent
Crawford

(10) Patent No.: US 6,560,488 B1
(45) Date of Patent: *May 6, 2003

(54) METHOD FOR ROTATABLY SECURING HEADPIECE TO THE HUMAN BODY

(75) Inventor: Scott Crawford, Castaic, CA (US)

(73) Assignee: Advanced Bionics Corporation, Sylmar, CA (US)

( * ) Notice: Subject to any disclaimer, the term of this patent is extended or adjusted under 35 U.S.C. 154(b) by 12 days.

This patent is subject to a terminal disclaimer.

(21) Appl. No.: 09/766,292

(22) Filed: Jan. 19, 2001

(51) Int. Cl.⁷ .................................................. A61N 1/08
(52) U.S. Cl. ......................................... 607/56; 607/57
(58) Field of Search ................................ 607/136, 137, 607/379, 55, 56, 57; 132/276, 277, 278, 280; 2/209; 128/903

(56) References Cited

U.S. PATENT DOCUMENTS 5,549,658 A * 8/1996 Shannon et al. ............... 607/57
5,775,345 A * 7/1998 Chou ........................... 132/278
6,275,736 B1 * 8/2001 Kuzma et al. ................. 607/57

* cited by examiner

*Primary Examiner*—Gregory Wilson
(74) *Attorney, Agent, or Firm*—Kenneth L. Green; Bryant R. Gold

(57) ABSTRACT

An improved hair-clip rotatably secures a headpiece of a Implantable Cochlear Stimulation (ICS) system adjacent to an implantable device of the ICS system. The hair-clip includes three fingers to securely grasp the headpiece around the cylindrical edge of the headpiece, while allowing rotation of the headpiece relative to the hair-clip. Both power and control signals are transmitted transcutaneously from the head piece to the implantable device. Efficient transmission of these signals requires that the headpiece be securely held in close alignment to the implantable device. The improved hair-clip securely holds the headpiece in place, and allows the headpiece to be rotated to position the headpiece cable. The ability to position the cable allows a user to achieve a comfortable and inconspicuous cable routing. The hair-clip also provides: retention regardless of skin flap thickness, secure retention during physical activity, and permits magnet-less retention thus minimizing interference with MRI examination.

24 Claims, 3 Drawing Sheets

METHOD FOR ROTATABLY SECURING HEADPIECE TO THE HUMAN BODY

BACKGROUND OF THE INVENTION

The present invention relates to implantable medical device systems, and more particularly to Implantable Cochlear Stimulation (ICS) systems. ICS systems are used to provide the sensation of hearing to those who are profoundly deaf, and for whom traditional hearing aids are of little or no assistance due to disease or damage to the middle ear or inner ear. An ICS system provides the sensation of hearing by applying electrical stimuli to the inside of the scala tympani duct of the cochlea, thereby directly stimulating the ganglion cells coupled to the auditory nerve. Once stimulated, such ganglion cells send nerve impulses to the brain through the auditory nerve, and the impulses are sensed in the brain as perceived sound.

ICS systems typically include implantable and external components. The implantable components include a receiver, an implantable pulse generator and an electrode array, which electrode array is inserted into the cochlea, through which the electrical stimuli are applied. The external components include a power source, a microphone, a speech processor, and a headpiece. The microphone senses sound waves in conventional manner and converts such sensed sound waves to an electrical signal. The electrical signal is then processed by the speech processor and converted into an appropriate control signal that is transmitted to the implantable receiver/stimulator. A representative implantable cochlear stimulation system is described in U.S. Pat. No. 5,776,172, issued Jul. 7, 1998 for "Multichannel Implantable Cochlear Simulator," incorporated herein by reference.

In operation, the power and control signals are transmitted to the implantable receiver/stimulator through a primary coil located in the headpiece, and are received through a secondary coil included within the implantable receiver/stimulator. In order to operate efficiently, i.e., in order for the headpiece to be able to transcutaneously (i.e., through the skin) transmit the control signal to the implantable receiver/stimulator, it is necessary that the primary coil in the headpiece be placed in close alignment with the secondary coil in the implantable receiver/stimulator.

The most common technique for retaining the headpiece of a transcutaneous-type implantable cochlear stimulation system is the use of two permanent magnets. One magnet resides in the implantable receiver/stimulator near the center of the secondary coil. The other magnet resides in the headpiece near the center of the primary coil. The use of magnets to retain the headpiece is very simple, effective, and cosmetically attractive. However, there are several drawbacks to this method of headpiece retention. Some users have thick skin flaps that increase the separation of the magnets and reduce their attracting force. Physically active children and adults have found magnetic headpiece retention insufficient. Additionally, the internal magnet may interfere with MRI (magnetic resonance imaging) diagnosis.

Another method of retaining a head piece is by using VELCRO® pads as described in U.S. Pat. No. 5,545,191, dated Aug. 13, 1996 for "Method for Optimally Positioning and Securing the External Unit of a Transcutaneous Transducer on the Skin of a Living Body." The '191 patent describes several embodiments with different shaped VELCRO® pads. While the use of VELCRO® pads provides some advantages, it also has several drawbacks. The use of VELCRO® pads to retain the headpiece requires that either the hook or loop VELCRO® pad be semi-permanently attached to the skin with several adverse results: the long term attachment to the skin of such pad may cause irritation or itching, the pads attached to the skin may be snagged when the user is combing or brushing their hair, the user's hair may also become tangled in the VELCRO® pads, and the extraction of the hair from the VELCRO® pads may cause significant discomfort. In addition to these ergonomic factors, the thickness of the VELCRO® pads may reduce the efficiency of the inductive coupling between the primary coil in the headpiece and the secondary coil in the implantable receiver/stimulator. Efficient power use in ICS systems is a significant issue, thus it is important that the primary and secondary coils be as close as possible. Further, if either the VELCRO® pad should become soiled, or if a user participates in work related or recreational activities that tend to soil or otherwise degrade the VELCRO® pads, frequent replacement of the VELCRO® pads may be required.

Yet another method of retaining a headpiece is using a hair-clip as described in U.S. Pat. No. 6,275,736 issued Aug. 14, 2001 for "Hair Clip Retention System for Headpiece of Cochlear Implant System," assigned to the assignee of this application. The '736 patent describes a hair-clip that avoids many of the disadvantages of a magnet retention system or a VELCRO® pad retention system. However, in some uses, the hair-clip of the '736 patent may result in the headpiece cable projecting from the headpiece case in an undesirable direction, wherein the cable may present a cosmetically undesirable appearance, or the cable may project away from the head and interfere with hats or snag on surrounding objects.

Therefore, there is a need for a low cost, robust, cosmetically acceptable, and comfortable alternative solution for holding the headpiece of an implantable cochlear stimulation system in close alignment with the secondary coil included in an implantable stimulator, that allows the headpiece to be rotated to a desired position.

SUMMARY OF THE INVENTION

The present invention addresses the above and other needs by providing an improved hair-clip for rotatably securing a headpiece of an Implantable Cochlear Stimulation (ICS) system, adjacent to an implantable device of the ICS system. The hair-clip includes three fingers to securely grasp the headpiece, while allowing rotation of the headpiece relative to the hair-clip. Both power and control signals are transmitted transcutaneously from a primary coil in the headpiece to a secondary coil in the implantable device. Efficient transmission of these signals requires that the headpiece be securely held in close alignment to the implantable device. The improved hair-clip securely holds the headpiece in place, and allows the headpiece to be rotated to position the headpiece cable.

In accordance with one aspect of the invention, there is provided an ability to rotate the headpiece relative to the hair-clip. The ability to rotate the headpiece allows a user to position the headpiece cable-to achieve a comfortable and inconspicuous cable routing. The improved hair-clip of the invention is adaptable to known headpieces, and results in a minimal cosmetic change.

It is a further feature of the present invention to provide retention of the headpiece regardless of the presence of skin flaps. A thick skin flap often results in excessive physical separation of the magnets in known ICS systems, thus preventing the magnets from attracting each other with adequate force to retain the headpiece in its desired position. The hair-clip does not rely on magnetic attraction of the headpiece to the implantable device, and thereby provides headpiece retention regardless of skin flap thickness.

It is an additional feature of the present invention to provide robust retention of the headpiece. Magnetic headpiece retention provides limited retaining force. When subjected to strenuous activities, magnetic retention is likely to fail to retain the headpiece. The hair-clip of the present invention may be used with magnetic retention, or alone, to provide adequate retention during periods of increased activity. When the invention is used in a magnet-less headpiece retention system, additional space is provided for electronics in both the headpiece and in the implantable device.

It is another feature of the invention to provide a headpiece retention method that does not require a magnet in the implantable device. The presence of a magnet in an implantable device may interfere with MRI examinations. The invention thus provides headpiece retention without such interference.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
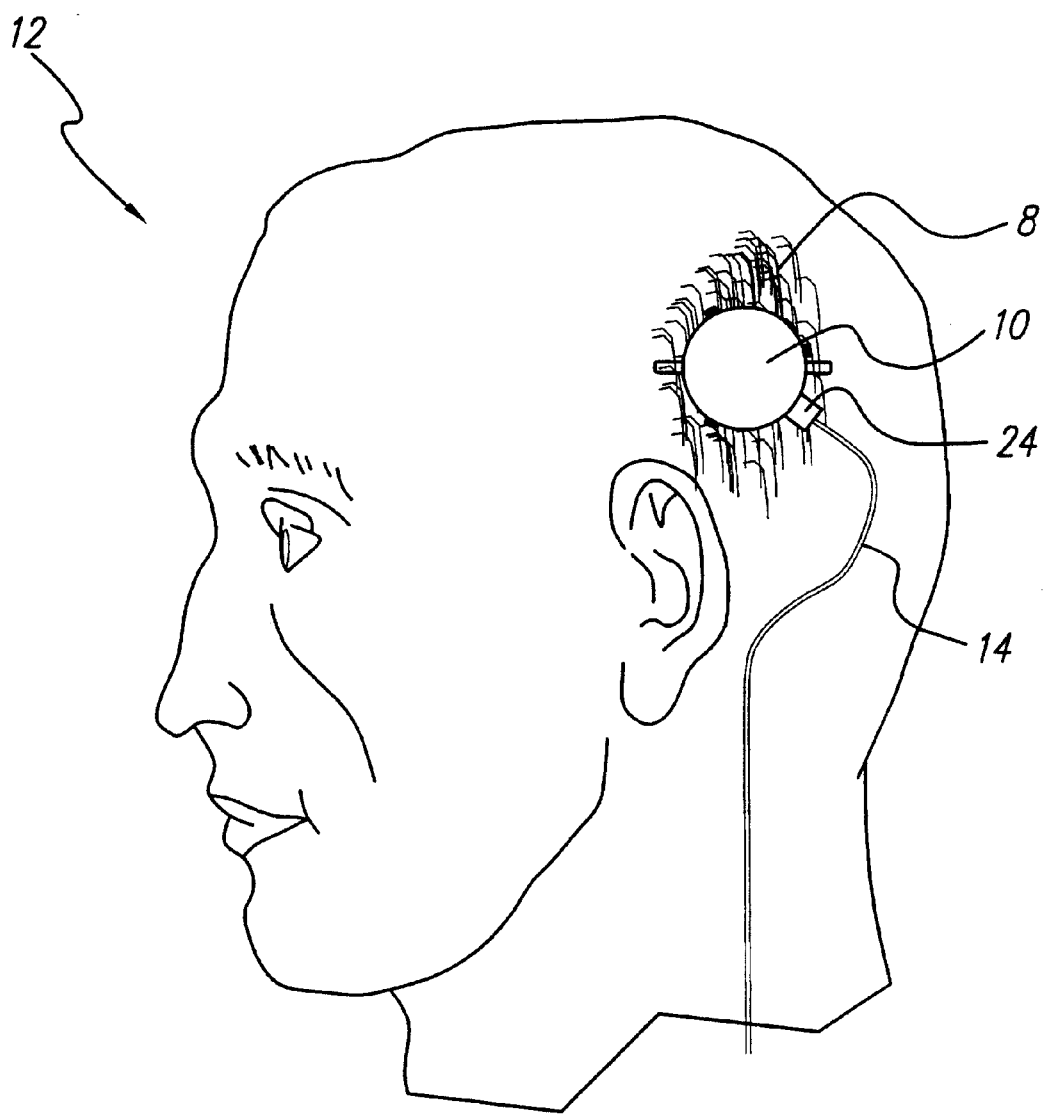
FIG. 1 depicts a headpiece retained on the head of a user by a hair-clip.

FIG. 1 shows a headpiece 10 held against the head of a user 12 by an attachment system of the present invention. The attachment system engages the hair 8 of the user 12 to retain the headpiece 10. A headpiece cable 14 is shown removably connected to the headpiece 10 by a connector 24, which connector 24 is attached to the headpiece 10.

Figure 2:
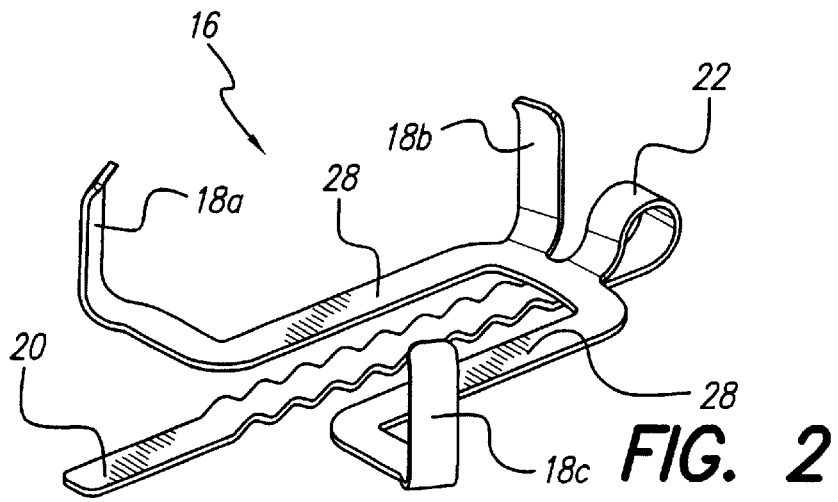
FIG. 2 depicts a hair-clip according to the present invention.

The attachment system of the present invention comprises a hair-clip 16 shown in FIG. 2. The hair-clip 16 comprises a hair-clip base and a means for rotatably attaching a headpiece to the hair-clip base. The hair-clip base comprises a headpiece support 28, a waved prong 20, and a spring member 22 springedly connecting the waved prong 20 to the headpiece support 28. The hair-clip base is removably and non-rotatably attachable to the hair. The hair-clip 16 is held against the head of the user 12 by capturing the hair 8 between the waved prong 20 and the headpiece support 28. The waved prong 20 is forced toward the headpiece support 28 by the spring member 22. Various functionally equivalent embodiments of the waved prong 20 and the headpiece support 28 exist. For example, a prong may or may not have waves, and the single prong shown in FIG. 2 may be replaced by two or more prongs. The prong may also be solid, or be a loop. The headpiece support 28 may also take on various shapes, and it is functionally sufficient for the prong and headpiece support to cooperatively engage the hair 8. Further, various other embodiments of the spring member 22 also exist. For example, other embodiments may include a spring and pivot arrangement. Any method of applying force (or torque) to the prong, in order to capture hair between the prong and headpiece support, comes within the scope of the present invention. The means for rotatably attaching a headpiece to the hair-clip base comprises three fingers 18a, 18b, and 18c. The cooperation of the fingers 18a, 18b, and 18c with the headpiece is described in FIG. 4 below.

Figure 3:
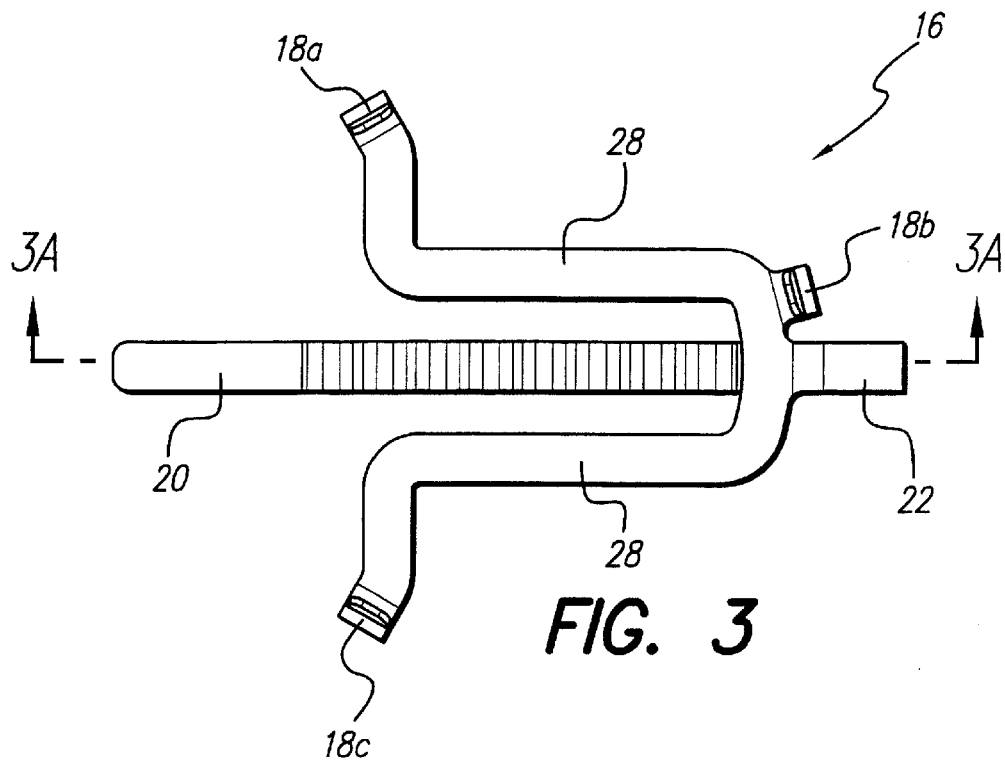
FIG. 3 shows a top view of the hair-clip.
Figure 3A:
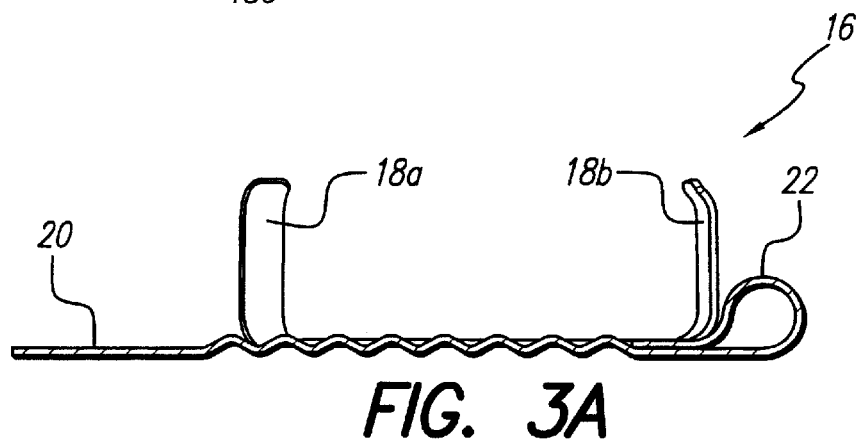
FIG. 3A shows a cross-sectional view of the hair clip taken along line 3A—3A of FIG. 3.

A top view of the hair-clip 16 is shown in FIG. 3, and a cross-sectional view of the hair-clip 16 taken along line 3A—3A of FIG. 3 is shown in FIG. 3A.

Figure 4:
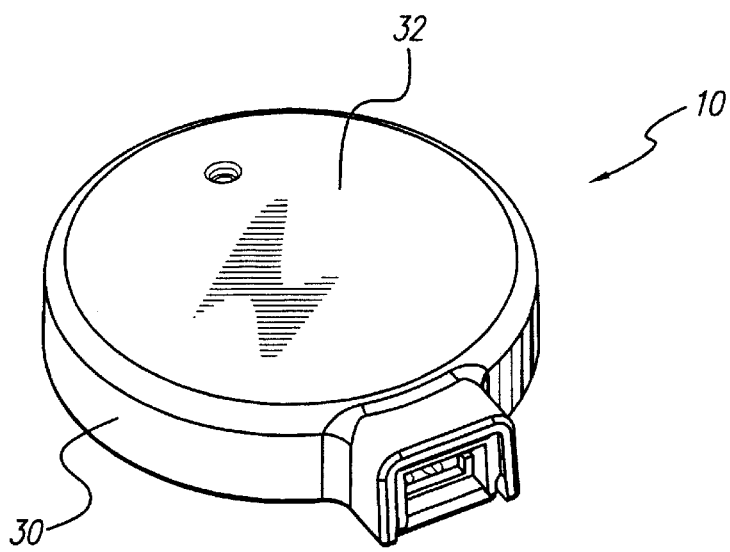
FIG. 4 shows a top perspective view of a headpiece.

The headpiece 10 detached from the hair-clip 16 is shown in FIG. 4. The headpiece 10 has a substantially cylindrical edge 30, and a rear face 32. A front face (hidden in FIG. 4) is opposite the rear face 32, wherein the front face resides substantially parallel and adjacent to the surface of the head when the ICS system is in use.

Figure 4A:
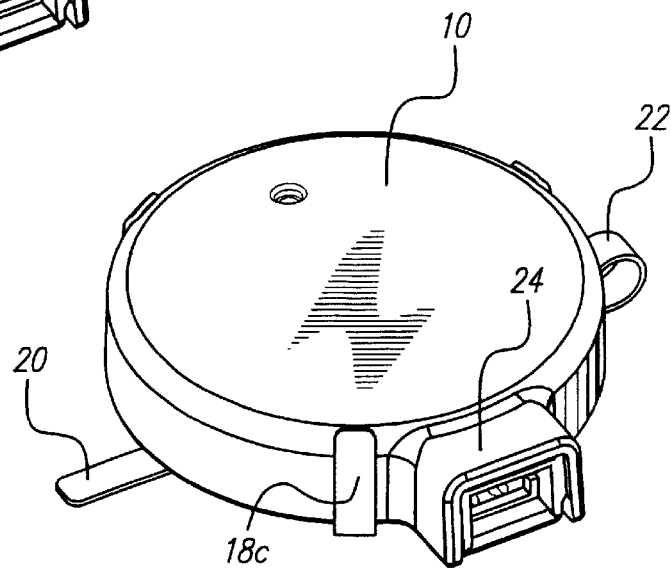
FIG. 4A depicts a top perspective view of the headpiece attached to the hair clip.

The hair-clip 16, with the headpiece 10 rotatably and removably attached, is shown in FIG. 4A. A primary coil in the headpiece 10 transmits control signals and power signals to a secondary coil in an implantable device. The control signals and the power signals are then processed by the implantable device to provide stimulation current to an electrode array implanted in the cochlea, which electrical stimulation results in the sensation of hearing. The fingers 18a, 18b, and 18c hold the headpiece 10 in the hair-clip 16 by reaching along the cylindrical edge and engaging the rear face. The connector 24 can be seen residing against the finger 18c. In this position, the headpiece 10 is prevented from rotating in a manner that would cause the connector 24 to move toward the finger 18c, but the headpiece 10 is free to rotate in the direction resulting in the connector moving away from the finger 18c.

Figure 5:
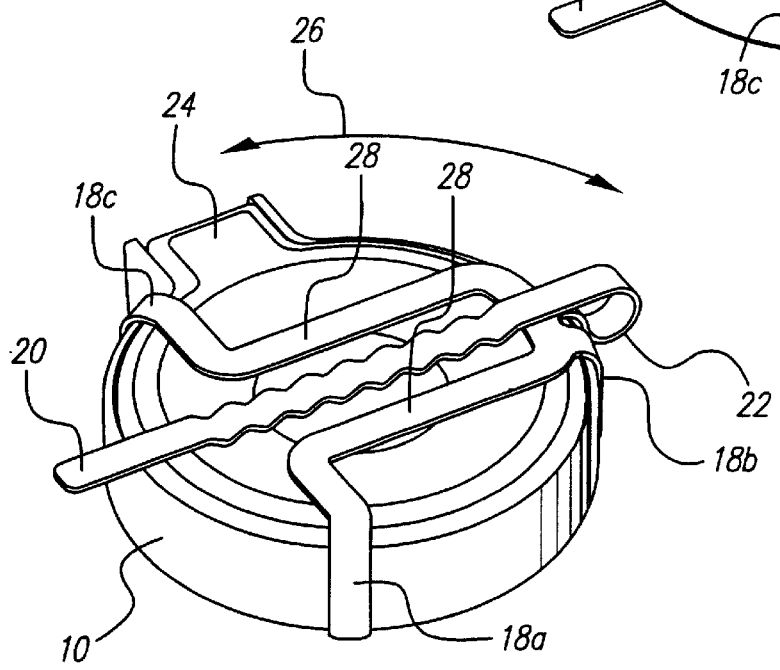
FIG. 5 shows a bottom perspective view of the headpiece attached to the hair clip, and depicts the rotational freedom of the headpiece.

Another view of the hair-clip 16 with the headpiece 10 attached is shown in FIG. 5. The arc 26 represents the possible movement of the connector 24 between the finger 18c and the finger 18b. The headpiece 10 could also be attached to the hair-clip 16 with the connector 24 between fingers 18a and 18b, or between fingers 18a and 18c. The position shown represents a more typical use. The spacing between finger 18c and finger 18b provides greater rotation than the other two possibilities, and also represents the most likely cable routing. In this position (i.e., when the connector is between finger 18c and finger 18b), the connector points down when the connector resides adjacent to finger 18c, and the connector points to the rear of the user when the connector resides adjacent to finger 18b.

The fingers may be positioned other than as shown in FIG. 5, or more fingers may be used. Such variations are intended to come within the scope of the present invention. There also may be variations to the shape of the headpiece, and those variations may require modifications to the fingers. Such variations and modifications are likewise intended to come within the scope of the invention. For example, if the headpiece is not round, the means for rotatably attaching a headpiece to the hair-clip base may comprise a rotatable member. The rotatable member is rotatably connected to a hair-clip base. The headpiece is non-rotatably attached to the rotatable member, and the headpiece is rotated by rotating the headpiece and rotatable member combination, relative to the hair-clip base.

As described above, it is thus seen that the hair-clip of the present invention eliminates the need for magnets in the headpiece and in the implantable device, provides secure attachment of the headpiece in the presence of thick skin flaps, and during periods of high activity, and allows the rotation of the headpiece to position the headpiece cable as desired by the user. The prong and finger arrangement of the hair-clip provides a simple and robust method for rotatable headpiece attachment. The use of the hair-clip also eliminates the need for a magnet in an implantable device, which magnet may interfere with MRI examinations.

While the invention herein disclosed has been described by means of specific embodiments and applications thereof, numerous modifications and variations could be made thereto by those skilled in the art without departing from the scope of the invention set forth in the claims.

What is claimed is:

1. A hair-clip for rotatably retaining a headpiece on the head of a user, comprising:
   a hair-clip base, wherein the hair-clip base is removably attachable to hair on the head of the user; and
   means for rotatably holding the headpiece on the hair-clip base, wherein the headpiece may be rotated relative to the hair-clip base.

2. The hair-clip of claim 1 wherein the hair-clip base is removably attachable to the hair by a prong, wherein the prong disengageably engages the hair, wherein the hair is grasped between the prong and the hair-clip base.

3. The hair-clip of claim 2 wherein the prong is a waved prong.

4. The hair-clip of claim 1 wherein the means for rotatably holding the headpiece on the hair-clip base comprises a multiplicity of finger extending from the hair-clip base.

5. The hair-clip of claim 4 wherein the multiplicity of fingers comprises three fingers.

6. The hair-clip of claim 4 wherein the headpiece has a substantially cylindrical edge, and wherein the multiplicity of fingers rotatably grasp the cylindrical edge.

7. The hair-clip of claim 1 wherein the headpiece includes a substantially cylindrical edge, a front face, and a rear face, wherein the front face resides substantially parallel and adjacent to the surface of the head, and wherein the means for rotatably holding the headpiece on the hair-clip base comprises means for slideably contacting the cylindrical edge and reaching past the cylindrical edge to slideably engage the rear face to rotatably hold the headpiece on the hair-clip.

8. The hair-clip of claim 1 wherein the means for rotatably holding the headpiece comprises a rotatable member, wherein the rotatable member is rotatably attached to the hair-clip base, and wherein the headpiece is removably attachable to the rotatable member, and wherein the rotational position of the headpiece is adjustable by rotating the rotatable member relative to the hair-clip base.

9. The hair-clip of claim 1 wherein a cable is connected to the headpiece, and wherein the means for rotatably holding the headpiece on the hair-clip base comprises means for rotatably holding the headpiece on the hair-clip base such that the position of the cable relative to the head may be adjusted.

10. The hair-clip of claim 1 wherein the headpiece is part of an Implantable Cochlear Stimulation (ICS) system.

11. A method for utilizing a hair-clip to rotatably retain a headpiece on the head of a user, comprising:
    attaching the headpiece to the hair-clip, wherein the hair-clip includes means for rotatably holding the headpiece wherein the attached headpiece may be rotated relative to the hair-clip; and
    attaching the hair-clip to the head of the user, wherein the hair-clip includes a prong, and wherein the prong disengageably engages hair on the head of the user to attach the hair-clip on the head.

12. The method of claim 11 wherein the hair-clip includes a multiplicity of fingers, and wherein the headpiece has a substantially cylindrical edge and a rear face, wherein:
    attaching the headpiece to the hair-clip comprises inserting the headpiece into the grasp of the multiplicity of fingers, wherein the multiplicity of fingers slideably contact the cylindrical edge and reach past the cylindrical edge to slideably engage the rear face.

13. The method of claim 12 wherein the multiplicity of fingers comprises three fingers, and wherein inserting the headpiece into the grasp of the multiplicity of fingers comprises inserting the headpiece into the grasp of the three fingers.

14. The method of claim 11 wherein attaching the headpiece comprises attaching the headpiece of an Implantable Cochlear Stimulation (ICS) system.

15. The method of claim 11 wherein the hair-clip includes a prong, and wherein attaching the hair-clip comprises disengageably engaging the prong with the hair of the user.

16. A removable hair-clip for rotatably holding a headpiece of an Implantable Cochlear Stimulation (ICS) system to the head of a user, comprising:
    a headpiece support;
    a prong springedly attached to the headpiece support, wherein the prong engages the hair of the user to secure the hair-clip to the head of the user; and
    a multiplicity of fingers attached to the headpiece support, wherein the fingers rotatably grasp the headpiece, wherein the headpiece may be rotated relative to the hair-clip.

17. The hair-clip of claim 16 wherein the prong is springedly attached by a spring member.

18. The hair-clip of claim 16 wherein the prong is springedly attached by a spring and a pivot.

19. The hair-clip of claim 16 wherein the multiplicity of fingers are adapted to cooperate with a substantially cylindrical edge and a rear face of the headpiece, and wherein the multiplicity of fingers slidably grasp the headpiece at a multiplicity of points around the cylindrical edge, and the multiplicity of fingers reach behind the rear face to rotatably hold the headpiece against the headpiece support.

20. The hair-clip of claim 16 wherein the headpiece may be rotated within the hair-clip to position a cable which is attached to the headpiece.

21. The hair-clip of claim 16 wherein the headpiece may be rotated to any position between a first position and a second position, and wherein a cable is connected to the headpiece, and wherein when the headpiece is in the first position the connector resides against one of the multiplicity of fingers, and wherein when the headpiece is in the second position, the connector resides against another of the multiplicity of fingers.

22. A removable hair-clip for rotatably holding a headpiece of an Implantable Cochlear Stimulation (ICS) system to the head of a user, comprising:

a hair-clip base;

a prong springedly attached to the hair-clip base, wherein the prong engages the hair of the user to secure the hair-clip to the head of the user; and a rotatable member, wherein the headpiece is removably attachable to the rotatable member, and wherein the rotatable member is rotatably held on the hair-clip base, wherein the headpiece and rotatable member may be rotated relative to the hair-clip base.

23. The hair-clip of claim 22 wherein the prong is springedly attached by a spring member.

24. The hair-clip of claim 22 wherein the prong is springedly attached by a spring and a pivot.

* * * * *